United States Patent [19]

Kiester

[11] Patent Number: 5,462,552
[45] Date of Patent: Oct. 31, 1995

[54] BONE CEMENT REMOVAL AND APPARATUS

[76] Inventor: P. Douglas Kiester, 2806 Westgate Ave., Los Angeles, Calif. 90064

[21] Appl. No.: 275,939

[22] Filed: Jul. 15, 1994

Related U.S. Application Data

[63] Continuation of Ser. No. 979,810, Nov. 20, 1992, abandoned.

[51] Int. Cl.$^6$ ............................................. A61F 7/00
[52] U.S. Cl. ........................... 606/92; 606/29; 606/30; 606/100; 606/99
[58] Field of Search ............................ 606/86, 99, 92, 606/93, 94, 100, 127, 128, 129, 27–31; 607/98, 99

[56] References Cited

U.S. PATENT DOCUMENTS

| | | | |
|---|---|---|---|
| 2,012,938 | 11/1934 | Beuoy | 606/29 |
| 2,200,322 | 8/1936 | Arnesen | 606/29 |
| 2,310,844 | 2/1943 | Draeger | 606/29 |
| 2,476,612 | 8/1946 | Lobdell | 606/29 |
| 3,886,944 | 6/1975 | Jamshidi | 606/27 |
| 4,108,181 | 8/1978 | Saliaris | 606/30 |
| 4,248,232 | 2/1981 | Engelbrecht | 606/27 |
| 4,702,236 | 10/1987 | Tarabichy | 606/99 |
| 5,041,120 | 8/1991 | McColl | 606/92 |
| 5,064,426 | 11/1991 | Huebsch | 606/92 |
| 5,151,099 | 9/1992 | Young | 606/27 |

Primary Examiner—Robert A. Hafer
Assistant Examiner—David J. Kenealy
Attorney, Agent, or Firm—Grant L. Hubbard

[57] ABSTRACT

An improved instrument for removing thermoplastic bone cement by applying a heater tip of heating wire to the cement to melt the bone cement inserting the hot heater tip into the bone cement, allowing it to cool embedded in the bone cement and to pull the instrument and, through the embedded heater tip, pull the bone cement from the bone.

17 Claims, 3 Drawing Sheets

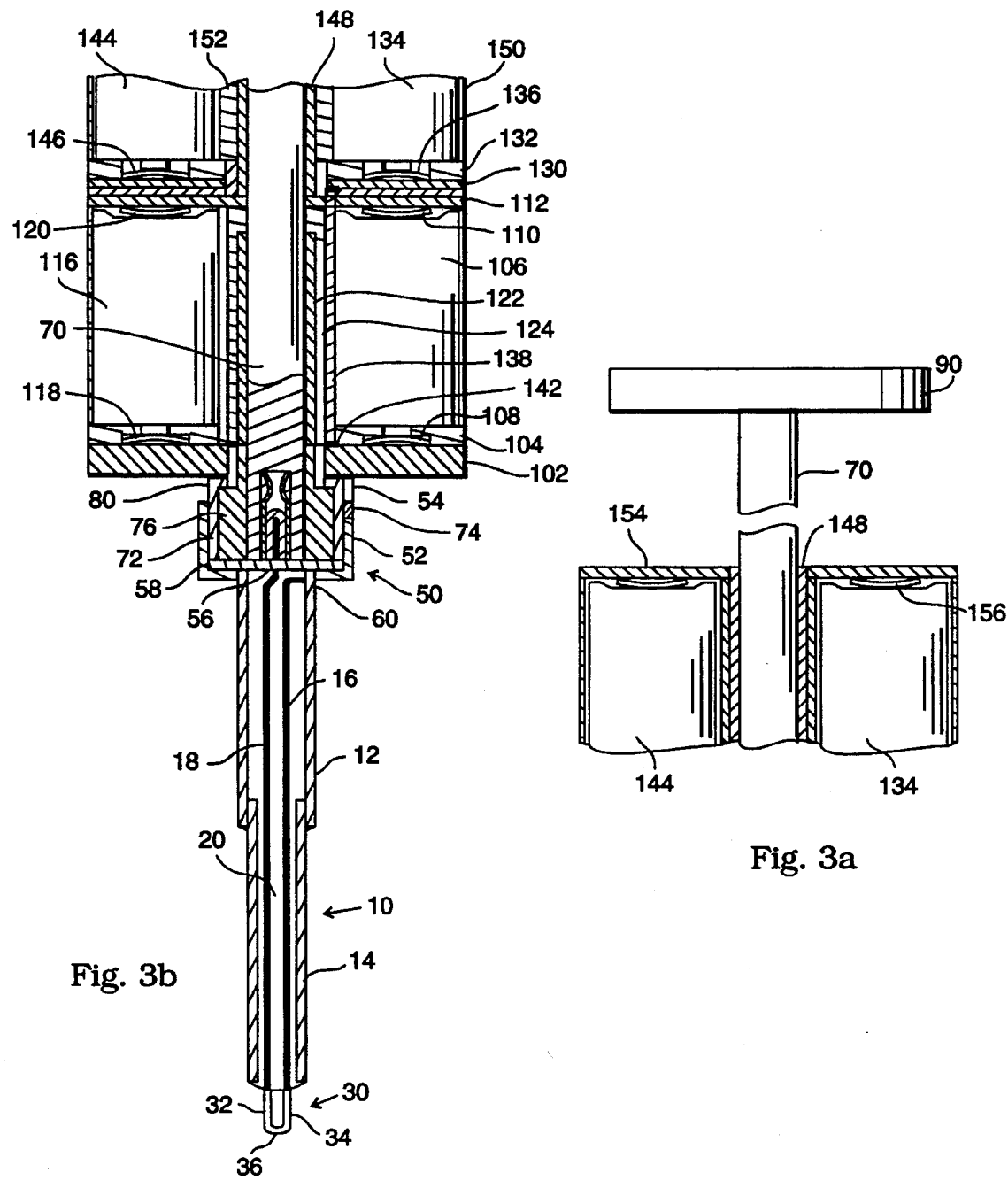

BONE CEMENT REMOVAL AND APPARATUS

This is a continuation of application Ser. No. 07/979,810 filed on Nov. 20, 1992, abandoned.

BACKGROUND OF THE INVENTION

This invention relates to orthopedic surgery and, more specifically, to the removal of bone cement in the repair or replacement of orthopedic prosthesis.

It is common practice in orthopedic surgery, particularly in the replacement of hip joints with prosthetic devices, to fix the anchor portion of the prosthetic device or devices in the bone using one or more types of bone cement. The most popular kind of cement currently in use is a methylmethacrylate based cement which can be mixed with the catalyst immediately before use and injected or placed around the prosthetic anchor in the bone where it quickly polymerizes and hardens to form a firm bond to the bone and to the implant. One such cement is sold by Dow Corning Wright, Arlington, Tenn. 38002, under the trademark CMW 3 the bone cement is sold in two packages, one consisting essentially of methylmethacrylate monomer, which contains stabilizers. The second portion is a mixture of polymethylmethacrylate powder and barium sulfate that contains a catalyst, or initiator, benzoyl peroxide. Barium sulfate is included as a radiopaque material so that the precise configuration of the cement, after it has set in the bone, can be determined by X-ray.

When the surgical procedure has proceeded to the point where the prostheses can be fixed in place in the bone, the first portion, which is a liquid, is mixed with the second portion. The second portion is in powder form and including small particles of polymethylmethacrylate which form nucleation sites for polymerization. The second portion also contains benzoyl peroxide which initiates polymerization quite rapidly. Once the mixing is complete, the surgeon has less than ten minutes in which to complete the use of the cement in the surgical procedure before it sets. Curing continues for several hours after set up, but the bone cement sets to a solid firm configuration in about ten to fifteen minutes. Once the cement is set, the surgical procedure can be completed while the curing of the cement continues.

Hot melt adhesives, i.e. thermal plastic materials which melt upon being warmed and harden upon cooling, may also be used, see Hayakawa, Y., et al, J. Takeda Res. Lab. (Japan), 1982, 41/1-2 (72–80).

The nature of the bone cement is of not critical to the present invention, except that it must be thermoplastic, that is, when the cement is set in place it must melt or soften upon the application of heat. Nearly all such cements are based upon the monomer methylmethacrylate, but any other meltable cement is subject to the method described hereinafter and can be removed using the apparatus which is described.

It is quite common that a prostheses must be removed after some period of use. Removal may be necessary because the prostheses has loosened, because of additional or separate injury, weakening of the bone in the proximity of the cement, or any of many other conditions. The removal of cement from a previously repaired joint or from around a previously installed prostheses presents a challenging problem to the surgeon. It is important that the cement be removed quickly, so as not to extend the time of the patient on the operating table to minimize trauma and lingering discomfort to the patient and discomfort to the surgical team.

The use of heated instruments to remove bone cement has been known for many years. Tarabichy, S. et al, U.S. Pat. No. 4,702,236, Oct. 27, 1987, describes several techniques for removing bone cement, including a method using a heated blade instrument for removing the bone cement. While the use of the heated blade obviates some of the problems inherent in prior art devices and methods, it still suffers from a number of disadvantages. Since it takes a considerable period of time to scrape even the melted cement from the bone using the knife blades of Tarabichy et al, the bone and adjacent tissue of the patient is heated considerably and it is possible to damage the bone and or the tissue upon prolonged heating. In addition, the heating of the cement generates noxious fumes which make it difficult for the operating team to perform. The fumes are lacrimators and may appear in the form of smoke which obscures the surgeons view.

Huebsch, D. L., U.S. Pat. Nos. 4,873,969, Oct. 17, 1989 and 5,064,462, Nov. 12, 1991 describes uses of a thermal chisel to remove bone cement. The thermal chisel described in Huebsch are internally heated by an electric heater. According to the Huebsch patent, the heated tip is inserted into the cement to mold one or more grooves in the cement. The heated tip is removed and the cement is allowed to reharden. Then the surgeon uses an impact chisel to break away the fragments of cement. The Huebsch method and apparatus suffers in the main from the same disadvantages that were noted with respect to the Tarabichy method; namely, the necessity for introducing large quantities of heat into the cement, because of the mass of the tools used and the nature and method in which they are used, the risk of overheating the bone and surrounding tissue and the length of time it takes to heat the tools and use them in the bone.

It is a principal feature of this invention to provide a method and an apparatus which can melt the bone cement to permit insertion of a retraction tool into the cement, allowing the retraction tool to cool in the cement and then extracting the tool and the cement.

Another object of this invention is to provide a disposable-self contained bone cement retraction tool which can be pre-sterilized and packaged so that no additional sterilization or further steps are required before use by the surgeon.

Another feature of the invention is the provision of an instrument which requires minimal amounts of energy to be introduced into the bone to obviate the risks of damage to the bone and surrounding tissues and the introduction of noxious fumes and smoke into the operating room.

SUMMARY OF THE INVENTION

The invention is an instrument assembly and system for removing thermoplastic bone cement from bones in replacement or corrective surgical procedures in which previously embedded thermoplastic cement needs to be removed. The instrument assembly comprises a loop formed of heating wire mounted rigidly in the proximal end of an elongated probe having proximal and distal ends. An electrical system is included in the assembly for supplying electricity to the loop for heating the same. Hammer means for applying an impact pulling force to the loop. The loop, probe, electrical system are so constructed, configured and connected as to permit the heating of the loop to a temperature sufficient to soften thermoplastic bone cement and, while heated, to be inserted into the cement by force applied through the probe. The loop of heating wire is allowed to cool, by removal of the electrical energy and, when cooled is embedded in the cement. The hammer means is constructed and configured to apply a cement removing impact pulling force to the loop for pulling the cement from the bone.

In a preferred embodiment, the loop is received in and heats a rod and an enlarged bead, which may be generally spherical or comprise a frustocone or otherwise be tapered or curved outwardly the rod, there being received about the rod a split end molly-bolt type structure. Upon being heated the molly-bolt structure, bead and rod are embedded in the cement. After only slight cooling, the hammer referred above is operated to exert a pulling, withdrawing force on the rod and bead, drawing the bead into the molly-bolt forcing the split end of the molly-bolt to expand outwardly gripping the cement and pulling it from the bone as the force is continued.

As an improved thermoplastic bone cement removing device, the invention is characterized in comprising a loop of heating wire, which preferably is in the molly-bolt and bead assembly, the heating wire being so constructed as to permit electrical heating thereof to a temperature sufficient to melt bone cement, to permit the loop to be inserted into the bone cement while heated, to be permitted to be cooled to thereby become embedded in the bone cement, and to permit the loop to be pulled thereby applying a pulling force through the probe and the loop to remove the cement from the bone.

The invention may be embodied in a self-contained, sterilizable thermoplastic bone cement removal system. The system comprises an elongated probe having proximal and distal ends, the proximal end constructed and configured to be inserted into a bone containing such cement to be removed with a loop of heating wire, as described, substantially rigidly mounted in and extending from the proximal end of the probe. An electric source and circuitry are provided for heating the loop to a temperature sufficient to soften the cement to be removed. The system also includes means for exerting a removal force through the probe and the loop and to the cement to be removed. The probe, loop, electric means and force exerting means are constructed and configured to selectively heat the heating element to a temperature sufficient to soften said bone cement and to permit the loop to cool embedded in the bone cement and to apply through the probe a removing force to the loop embedded in the cement for removing such cement from such bone. Unlike all prior art devices, the invention utilizes a loop or, preferably, a molly-bolt and bead assembly, that can be heated and embedded in a mass of thermoplastic bone cement.

BRIEF DESCRIPTION OF THE DRAWINGS

FIG. 3a is the distal or upper portion of the apparatus of this invention shown in partial cross section, taken vertically substantially in the center thereof.

FIG. 3b is the lower or proximal portion of the device of this invention also in partial cross section taken substantially along the center of the device.

DESCRIPTION OF THE PREFERRED EMBODIMENTS

The following description is given in considerable detail and relates to the prototype which was made and tested. Product engineering giving details to methods of production, optimizing materials and minimizing costs, etc, will undoubtedly result in some changes in the general configuration and in various components of the invention and such is contemplated in the following description. In addition, specific examples of methods of accomplishing particular goals, i.e. insulating one portion from another, etc, are provided in order to give a complete disclosure of the operating prototype. Many alternatives are available for some of these fairly well known structural relationships and it is not the intent of this specification and description to limit the invention to these particular details. Great latitude is given to design engineers and artisans in the manufacture of commercial embodiments of the invention.

Figure 1:
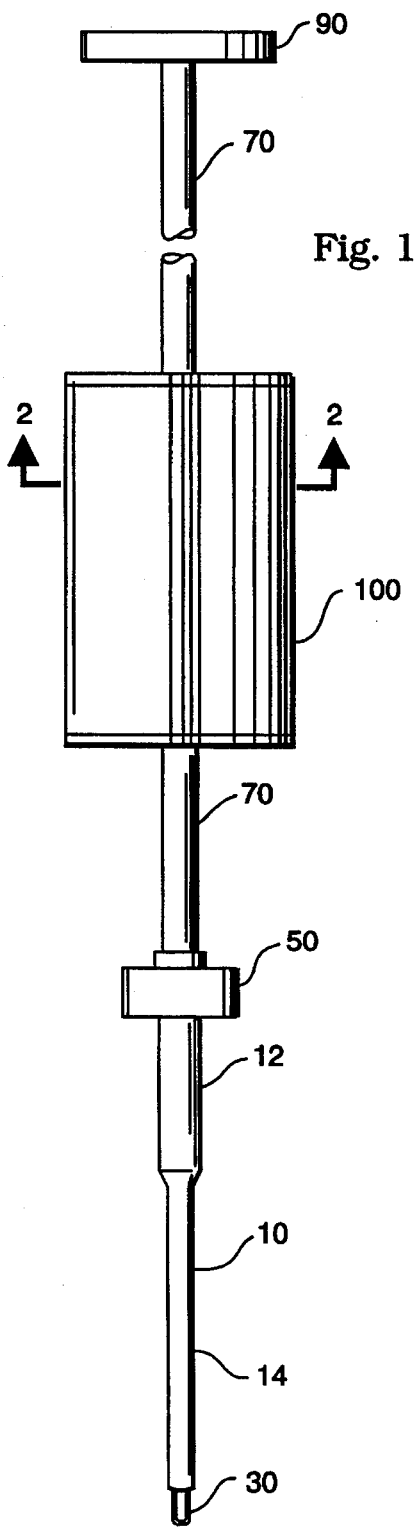
FIG. 1 is a side view of the overall apparatus of this invention showing the relationship of the major components thereof.

Referring first to FIG. 1, the overall construction and operation of the invention can be described. The invention comprises a probe assembly 10 which in this particular embodiment involves a larger distal sleeve and a smaller proximal sleeve which, with other structures to be described, support a tip assembly 30 which is used for actually contacting of the cement and removal thereof, as will be described. The sleeve assembly is connected by a bayonet connector or some other type of electromechanical connector to the hammer shaft assembly 70, having hammer striker means in the form of a distal hammer disk 90 at the most distal end of the device. The battery assembly 100 is slidably mounted on the hammer shaft 70 for reciprocal movement. Without mentioning particular techniques and constructions, the mode of use of the invention is as follows:

The sleeve assembly is inserted into the bone such that the tip 30 is in contact with or near the bone cement the battery hammer assembly 100 is moved to a proximal most position, resting against the connector assembly 50 in which position it provides electrical energy through conductors to the tip. The tip is constructed in the manner to be described such that only the tip is heated and most of the heat is generated in the bridge portion between the two legs of the tip which is shaped to form a cutting edge. This heated cutting edge is pushed into the heated cement, as only a small portion of the cement is melted. The surgeon can easily recognize the amount of movement indicating insertion of the tip into the cement. Once the tip has melted the cement and moved into the cement, then the battery hammer assembly is removed from its contact with the connector 50, disconnecting electrical energy from the tip whereupon the tip cools. The tip is in the form of a loop having two extension portions and a bridge portion. Being in the form of a loop it is entrapped in the cement and bonded thereto. The surgeon then uses the battery hammer assembly in a well known manner, slamming it vigorously against the distal hammer disk exerting strong shock removal forces on the cement. In most instances, the cement plug surrounding the tip comes out as a single plug. Sometimes the process has to be repeated several times.

It is possible of course that the cement be so anchored in the bone that it cannot be removed as a plug. When this occurred with some prior art devices, the tool was locked firmly into the cement and the surgeon had the additional challenge of removing the tool before further attempts could be made to remove the cement. With the present invention, if the force which can be exerted by the present invention is insufficient to remove the cement plug, the bridge of the tip simply breaks, releasing the tip from the cement and the entire assembly is removed from the bone. Further attempts with new tips can be made or the more tedious prior art process is resorted to.

Again with the caveat that the following details are provided to assist in understanding the invention and to disclose the best mode know to the inventor at the present time and not as limiting the invention, the detailed construction of the invention will be described.

Figure 4:
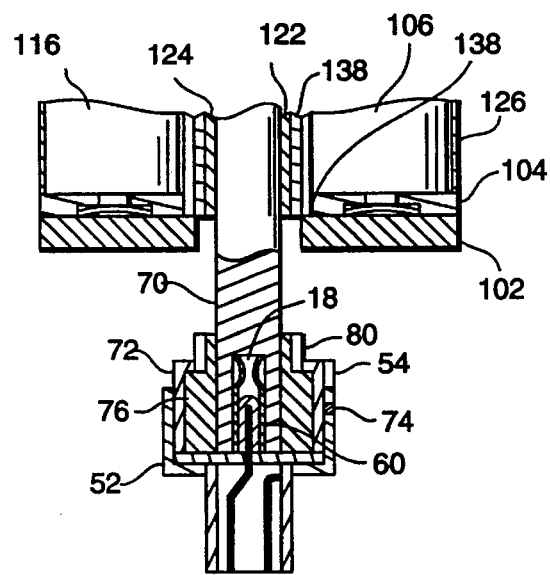
FIG. 4 is a depiction of the electrical interconnect system and mechanical interconnect system between the hammer shaft, the battery hammer assembly and the probe assembly of the invention.

Reference is now made principally to FIGS. 1, 3b and 4, principal reference being immediately made to FIGS. 1 and 3b.

The probe assembly 10 comprises a distal sleeve 12 and a proximal sleeve 14. Carried inside the sleeve are first and second electrical conductors 16 and 18 which are mounted in the sleeve, electrically separated from each other, and mechanically secured firmly in the sleeve by a refractory insulation 20. The refractory insulation in the preferred embodiment is a particle filled, electrically nonconductive, thermally insulator resin which has a high enough heat resistance to avoid damage by the heats used in melting bone cement. Filled epoxy resins may be quite satisfactory in this application. Traditional alumina based or silica based potting agents may also be used. The term "refractory insulation" is used here to mean that the potting material is strong enough to bond the conductors and the tip loops securely in the sleeve and sufficiently heat resistant so as not to be damaged. Within that broad parameter, many types of potting agents, cements and adhesives may be used. In mass production, the use of adhesives and potting materials may be minimized or avoided by using pre-manufactured components specifically designed to be assembled in a structure substantially as shown and described. Indeed, production versions of the present invention are expected to comprise a probe assembly formed of graphite fibers or glass fibers bonded with a high temperature resistant bond or fused together that support the electrical conductors.

The tip or loop assembly 30 comprising a first and second tip extensions 32 and 34 and a bridge 36, the bridge being so constructed as to form a cutting edge and to provide the highest electrical resistance when the tip or loop is connected to a source of electrical energy.

Figure 5:
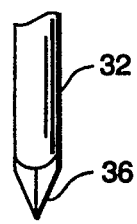
FIG. 5 is a greatly enlarged side view of the heated tip used in this invention.
Figure 6:
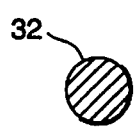
FIG. 6 is an enlarged cross section of one portion of the heated tip assembly of this invention.
Figure 7:
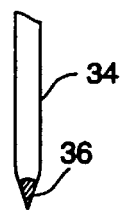
FIG. 7 is a cross section of the very tip, the cutting edge that is heated in use, of the tip assembly of this invention.

Reference is made now briefly to FIGS. 5, 6 and 7 for a detailed description of the loop. FIG. 5 is a side view of the loop showing one of the loop or tip extensions, the first extension 32 and the bridge portion 36. It will be noted that the bridge portion forms a cutting edge at the forward end thereof.

As shown in FIG. 6, the cross sections of the extensions are circular. Of course, any other cross section may be used, but circular cross sections are most easily obtained and most inexpensively available. Viewing FIG. 7 and comparing it with FIG. 6, the cross section of the bridge 36 will be seen to be substantially smaller than the cross section of the tip extension 34. Thus, the bridge forms a cutting portion and, having a smaller cross section, will also provide the highest resistance to the flow of electric current and, hence, will be heated most rapidly upon the application of electrical energy. A square cross section or a diamond shaped cross section tip could also be used and would inherently provide a cutting edge. Also, it is not absolutely necessary that the cutting edge cross section be less than that of the rest of the tip. The invention will perform satisfactory if the cross section of the tip heater is uniform, but far greater efficiency is obtained using a bridge portion at the extreme distal end which is both a cutting edge and a reduced cross section to provide the higher heat generation.

Figure 8:
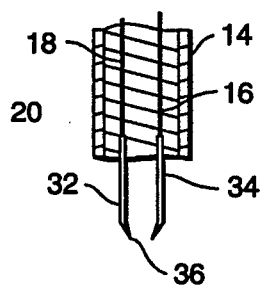
FIG. 8 shows the tip assembly with the tip broken to illustrate one of the safety features of this invention.

While discussing the tip, reference is also made to FIG. 8 which shows a tip identical to that shown in FIG. 3b, except that the bridge portion 36 has been broken. An additional advantage of configuring the bridge portion or the distal most end of the heater to have a smaller cross section is that if the cement is to firmly lodged to be removed using the present invention, then the bridge portion simply breaks and the two can be removed. Indeed, the two will automatically be removed in the course of carrying out the method if the cement is too firmly lodged to be removed by the method as described.

Figure 9:
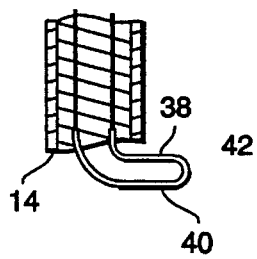
FIG. 9 illustrates an alternative configuration of the tip assembly of this invention.

FIG. 9 depicts a tip of an alternative configuration in which the tip extensions 38 and 40 extend laterally, generally perpendicularly to the axis of the probe and the extreme bridge portion of the tip 42 is to the side rather than aligned with the probe. This configuration is useful in removing small pockets and blocks of cement which are bonded to the side of a passage in the bone or in a cavity which is accessible only from the side. Obviously, the angle at which the tip can extend from the probe is subject to infinite variation. Other than the direction in which the tip is moved to melt the cement, the operation is the same.

Referring now to FIGS. 1 and 4 in particular, the probe assembly is connected to the hammer shaft assembly by means of a bayonet connector 50. A screw type connector or any other kind of connector will perform equally well but a bayonet connector provides for a quick and reliable connection. The female portion of the bayonet connector 52 is connected to the top of the distal sleeve. The bayonet connector portion 52 is provided with a slot arrangement 54 as is common in bayonet connectors. This generally "L" shaped slot and the bayonet connector performs in the manner typical of such connectors. The female portion of the bayonet connector may be connected by a weldment 56 or by an adhesive bond, a screw fitting or any other suitable and convenient fitting. An insulating disk 58 rests at the bottom of the interior opening of the female portion 52 of the bayonet connector and carries on it a conductive pin 60 which provides for electrical connection between the heater tip and the battery hammer assembly.

The male portion of the bayonet connector 72, carrying the usual bayonet connector pin 74, secures by means of an adhesive or potting compound 76 the proximal end of the hammer shaft 70. The distal end of the shaft has an aperture formed in it and a resilient electrical dip 78 is fitted into the aperture. It is not necessary to provide for a resilient clip inside the aperture, it is quite satisfactory simply to provide an aperture in the shaft which fits in electrically conductive relationship with the electrical conductive pin 60. However, more certain connection is provided by a spring dip.

The upper most end, as viewed in the drawings, or the distal end of the male portion of the bayonet connector 80 forms an upwardly extending sleeve which provides electrical contact with the battery hammer assembly. The sleeve 80 is separated from the shaft 70 by means of the insulating potting compound 76. The potting compound may be an epoxy resin or any other potting compound, may be filled or unfilled, and may be high temperature resistant but need not be so. The same kind of potting compound may be used in the probe and in the bayonet connector, but this is not necessary.

Referring now to FIGS. 1 through 4, a detailed description of the prototype embodiment of the battery hammer assembly is provided. It will be understood that the prototype was made up of existing components that were readily available. It is expected that when the product is engineered for commercial production it will be simpler and probably smaller than indicated in the drawings and in the following description.

The battery hammer assembly 100 comprises at its proximal end a proximal collector plate 102 which has formed therein a female connector aperture which, during heating, is in electrical contact with the sleeve 80 thereby providing electrical contact from the batteries to the heating element as will be described. A plurality of "C" cells or "D" cells may be used. In order to provide some shock absorption to prevent damage to the cells, a disk 104 may be provided. The disk is not necessary but is desirable in the particular configuration described. Again, it is contemplated that a specially designed cylindrical battery may be used with far greater efficiency and ruggedness. Indeed, any kind of electrical package may be provided.

The cell 106 is electrically connected to the collector plate 102 through a Belleville washer shock absorbing spring type electrical contact 108. Obviously, any kind of electrical contact would be suitable but the Belleville washer is a convenient construction. Another Belleville washer 110 is provided at the negative end of the cell 106 and connects the negative end of the cell to the collector plate 112. In an analogous manner, the cell 116 is connected through a Belleville washer 118 to the positive collector plate 102 and through a Belleville washer 120 to the negative collector plate 112. Four such cells are provided in a symmetrical arrangement around the hammer shaft in the prototype embodiment. The number and size of cells and the voltage and current requirements are a function of the heater and, of course, there is no particular criticality to the number or size of cells or batteries used in the invention.

The positive collector plate 102 is in electrical contact with the sleeve 80 and through the bayonet connector portion 72 is in electrical contact with the female bayonet connector portion 52 which, in turn, is an electrical contact, by welding, brazing or otherwise, with the sleeve of the probe. However, in the preferred embodiment, the sleeve is not used for conducting the electricity to the heater tip, although it could be. It has been found most desirable to provide a low electrical resistance conductor 16 which is secured by welding or otherwise to the bayonet portion 52 as indicated by the weldment 60.

The negative collector plate 112 is in electrical with the hammer shaft 70 through a guide sleeve 124, the lower portion of which may be separated from the shaft by means of an insulating sleeve 122. The insulating sleeve is not necessary if adequate electrical insulation is provided at the proximal end. All that is necessary is that the negative collector plate be an electrical contact with the shaft and that the shaft and negative collector plate be electrically isolated from the positive collector plate 102, the bayonet fitting and the conductor 16. It is recognized that the prototype is perhaps somewhat complex and more complex than will be required in production, but it is the best mode presently used by the inventor.

An insulating and shock absorbing washer 132, analogous to washer 104, is used to prevent damage to the cell 134 which is connected through a Belleville washer 136 to the positive collector plate 130 and, referring to FIG. 3a through a Belleville washer 156 to the negative collector plate 154. An electrical conductor 138 is connected by a weldment 140 and a weldment 142 to the positive collector plates 130 and 102, respectively. Of course any kind of electrical connection may be used and any kind of conductive coupling between the positive collector plates may be used. Indeed, if only one cell is used there is no need for the collector plate assemblies at all. The cell 144 is likewise supported for shock resistance by the spacer disk 132 and is connected at the positive end through the Belleville 144, shown in FIG. 3b and at the negative end through the Belleville washer 158 as shown in FIG. 3a to the positive and negative collector plates, respectively.

The guide sleeve 148 is conductive and is connected to the negative collector plates 154 at the distal end and 112 at the proximal end.

Figure 2:
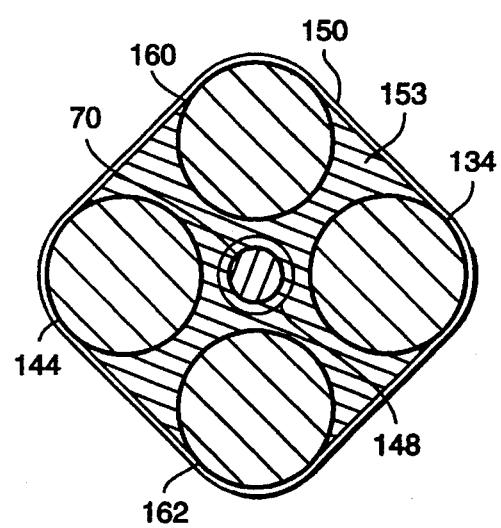
FIG. 2 is a cross section of the battery hammer assembly of the device of this invention taken substantially along lines 2—2 in the direction of the arrows.

Referring momentarily to FIG. 2 in particular, a compression sleeve 150 is provided and a filler stabilizing block 152 may also be provided. It has been found that when the battery hammer assembly is used as a hammer the electrical cells sometimes rupture simply because of the force exerted. The relatively thin walls of the cells are not designed for high impact. In order to prevent these ruptures, a compression 150 has been provided around the distal most set of cells and a compression sleeve 126 has been provided around the proximal most set of cells. In addition, if desired, a stabilizing block 152 with cavities sized to receive the cells. With this arrangement, the force exerted on the thin battery wafts of the various cells is transmitted directly to the supporting structures and the cells maintain their integrity. Again, it is recognized that in engineering the product for commercial production one or more cells with walls designed to stand up to the forces of using the battery hammer assembly as a hammer may be used rather than the comparatively complex arrangement described. In principle, however, the same construction will be used.

Still referring to FIG. 2, it will be noted that in the illustrative embodiment, which is similar to the prototype which has been constructed and tested, four cells are arranged symmetrically. The cells 134 and 144 are on opposite sides of the shaft 70 and cells 160 and 162 are intermediate to the other cells and on opposite sides of the shaft 70. While not shown, a similar arrangement is provided in the proximal set of cells. This provides, in this particular embodiment, eight C cells connected in parallel to provide a high burst of current to provide virtually instant heating of the tip. The design of the tip and the providing of a source of electrical energy is, of course, a very routine matter for electrical engineers and a virtually infinite variety of alternative configurations may be used to accomplish the purpose and would be identical in theory and equivalent in construction and operation and result with that described in the specification.

The entire apparatus may be sterile packaged and additional tip assemblies my be in separate sterile packs to permit the surgeon to select the tip or tips of the size and configuration desired.

Having described the construction of the presently best known embodiment of the invention, embodied in the prototype, a more detailed description of the operation of the invention is possible.

First of all, it will be recognized that about the only thing that is critical about the apparatus is the arrangement and structure of the tip. Virtually any shape or size of probe may be used, any source of electricity may be used any kind of hammer may be used, etc.

The tip comprises a loop formed of wire having a high resistance, compared with copper or aluminum wire, referred to in the industry and here as heater wire. Nichrome wire, a nickel and chromium containing wire, is very widely used as a heater wire in electrically energized radiant heaters. Nichrome®, which has an electrical resistivity of about 100 microhm centimeters at 20° C. and a melting point of 1300° C. is highly suitable for use in the present invention but any other wire which will heat quickly when energized with an electric current may be used. Copper wire is the preferred electrical conductor material because of its low resistivity, under 2 microhm centimeters, low cost and readily availability. The heater wire must have a resistivity of at least about ten times the resistivity of the electrical conductor wire to operate with reasonable efficiency. (An poor but generally equivalent approach is to design the heater wire of a lower resistivity material, perhaps even copper, and make the heater loop of very, very much thinner wire to increase the effective resistance of the loop as compared with the conductor.) The fifty to one ratio the resistivity of Nichrome® to copper wire offers a nearly ideal paring of materials. The heater wire must heat quickly to avoid introducing large amounts of heat into the bone and surrounding tissue. The loop may be of any size small enough to enter the bone and the cement, and may be of different shapes. The optimum size and shape also depends to some extent on the size of the cement mass to be removed. A pre-sterilized kit typically will include a number of probes each with a different tip size and/or shape. Generally a loop having a pair of parallel straight tip extension wires from 0.1 to 0.5 inches apart, typically from 0.25 to 0.375 inches apart, joined at the proximal extremity with a generally arcuate bridge formed to define a cutting edge at the leading edge. The wire diameter is variable. The wire must, however, be stiff enough to hold the loop shape as the hot loop is forced into the cement. Nichrome wire, 14–18 gauge, having a total length of from about 1 to about 4 inches, forming a loop about 0.5 to 1.5 inches long with the tip extensions being straight and parallel, spaced about 0.2 to 0.4 inches apart, with the forward edge, the extreme proximal portion, of the bridge defining a cutting edge, that will heat in about 5 to 10 seconds to a temperature of about 160° C. to about 250° C. upon the application of 1.5 volts is an optimum arrangement for most applications.

The tip must be connected to electrical conductors capable of carrying electrical current to the heater wire of the tip without significant increase in temperature of the conductors. The sleeve may be made of a highly conductive metal or alloy or include such and alloy and serve as one of the conductors; however, it has been found most advantageous to use two distinct copper conductors. The connection with the conductors must be stable at temperatures up to about 200° C. to 250° C. to retain electrical continuity during use. A welded, silver soldered or firm mechanical connection may be used. A strong mechanical connection is also desirable between the copper wire and Nichrome® wire. Interlooping the ends of the respective wires and welding the loops together is a preferred connection. Nichrome® wire of 16 gauge resistance of 0.085116 ohms/cm while copper wire of the same gauge has a resistance of 0.000132 ohms/cm. Such a high difference in resistance permits optimization of the wires in the general range of 14 to 18 gauge. Obviously, however, a larger conductor wire may be used to minimize heat losses.

The tip must be reasonably rigidly mounted in the proximal end of the probe to extend from the probe and too transmit mechanical force from the probe to permit the surgeon to force the heated tip into the cement. The tip may extend axially of the probe, which typically is a cylinder having an axis and one or more diametrical dimensions, or perpendicular to the axis of the probe or at any other desired angle relative to the axis of the probe that may be necessary or convenient to permit the heater to be forced into a body of cement. Some structural rigidity can be obtained, without effecting the electrical characteristics of the probe, by extending the heater wire some distance, from one to five or more centimeters, into the probe potting beyond the point of electrical connection.

The probe may be of any configuration that will permit the surgeon to position the heater tip against the cement and force the tip, when heated, into the cement. An elongated cylindrical configuration is optimum for convenient and economical manufacture. The probe length is not critical. A probe length of from about six inches to 15 inches is optimum for most uses, but any length of probe may be used.

Any source of electric energy may be used. Means may be provided for conducting electricity from a standard wall outlet to the tip, for example. There is, however, a distinct advantage in providing a fully self-contained surgical appliance that does not require any external power source. Wires in or near the surgical site are avoided, the entire unit may be sterilized and positioned at will if the apparatus includes a power source for heating the tip. One of the very important and useful features, though not an essential feature, of the invention is the provision of a combined battery pack and hammer that provides the electrical energy and the mechanical force needed to remove the cement.

The combination of the hammer shaft 70 with the distal hammer striker means 90 and the battery hammer assembly 100 is a great advantage. As described, the battery hammer assembly 100 is moved proximally reciprocally on the shaft 70 to the maximum proximal position where it electrically engages the electricity input to the probe and tip thereby heating the tip. The battery hammer assembly 100 serves as a handle for pushing the tip into the cement and as a source of electricity heating the tip and melting or softening the cement. As soon as the heated tip is pressed into the cement, the battery hammer assembly 100 is moved distally reciprocally removing electric energy from the probe and tip, allowing the tip to cool embedded in the cement. After a short cooling period, one-haft minute to two minutes usually being sufficient, the battery hammer assembly is slid rapidly distally to the distal extreme where it strikes the distal hammer disk transmitting the kinetic energy of the heavy battery hammer assembly to the hammer shaft and, ultimately, to the tip to apply a pulling, removal force thereto. If the force is great enough, the cement simply slips out of the bone, if it can be moved. If the cement mass is locked by its configuration into the bone, then the bridge portion of the tip ruptures, as shown in FIG. 8, and slips out of the cement. If there is doubt, or if not all the cement came out, the process can be repeated as many times as needed. Thus, the removal tool is never lodged in the cement, a great advance over the prior art.

Figure 10:
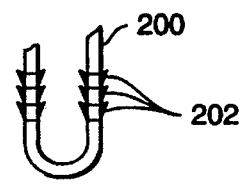
FIG. 10 depicts an alternative form of heated tip.

Various alternative tip designs may be used. For example, the tip design depicted in FIG. 10 comprises nichrome or other heater wire 200 having formed thereon threads or flutes 202 formed on the surface thereof and extending outwardly to provide greater gripping power.

Figure 11:
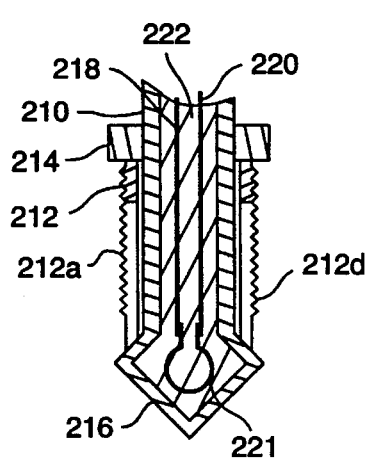
FIG. 11 depicts a alternative form of tip assembly comprising a heatable tip and an expandable molly-bolt type sleeve.
Figure 12:
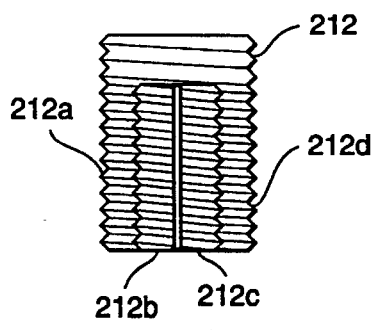
FIG. 12 depicts the expandable molly-bolt type sleeve of the assembly shown in FIG. 11.
Figure 13:
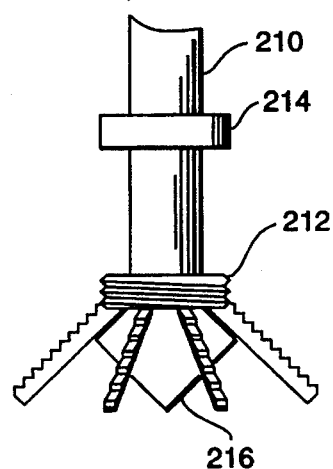
FIG. 13 depicts the heater assembly of FIG. 11 which comprises an expandable molly-bolt type sleeve, the sleeve being shown expanded.

In addition, an expandable tip assembly may be used. One such exemplary expandable tip assembly is shown in FIGS. 11, 12 and 13. The tip assembly comprises a tube, or equivalent elongate support, 210 which has slidably received thereon a threaded or fluted molly-bolt type cylindrical sleeve 212 which has two or more splits in the distal portion thereof forming expandable portions 212a, 212b, 212c, and 212d, as shown in more detail in FIG. 12. A retainer 214 secures the fluted, expandable sleeve 212 proximate an enlarged distal tip 216 into which the heater wire, which is connected to the electrical conductors 218 and 220, extends supplying heat to the tip, tube and molly-bolt sleeve. Alternatively, the tip may be made of Nichrome®, or other high resistivity material, with the connectors connected thereto, by welding for example. Upon application of electricity the tip is heated and the heat is conducted to the tube and sleeve. In use, the tip is heated and inserted into the cement to be removed. When the tip is moved outwardly, the flutes or threads on sleeve 212 engage the cement causing the enlarged tip 216 to be pulled into the sleeve whereupon the portions 212a– 212d, and other such portions, expand gripping the cement more tightly, as shown in FIG. 13. In this embodiment, very little cooling time is necessary because the molly-bolt type sleeve expands outwardly into unmelted cement. Indeed, the cooling time may be omitted entirely in some procedures.

The terms "melt" or "melting" are used to mean the softening of the thermoplastic cement, recognizing that such cements have a broad transition temperature range in which they change from solid to a very viscous liquid to a moderately viscous liquid. It is not necessary that the cement reach the full liquid state upon application of the heated loop; it is sufficient that the thermoplastic cement be softened enough to be penetrated by the hot loop and be permitted to be cooled embedded in the cement, i.e. engaged in the cooled cement to exert a pulling force on the cement in which it is embedded.

The battery hammer assembly shown includes two sets of four "C" cells all connected in parallel. In practice, one set of four "C" or "D" cells works satisfactorily; however, to illustrate a somewhat more complex embodiment, two sets of four cells was shown. The cells may, of course, be connected electrically to provide the voltage and current necessary to heat the tip. For example, the cells may be connected to provide 3, 4.5 or 6 volts. As mentioned before, it is anticipated that in production engineering a specially configured cell or battery will be designed to provide suitable current and voltage in a mechanically sturdy package at an economical cost.

The instrument assembly of the invention, thus, comprises a loop formed of heating wire substantially rigidly mounted on the proximal end of an elongate probe an electrical system for heating the loop and means for applying a removal force through the probe and loop to thermoplastic bone cement. The removal force is preferably a striking impact force applied by a slide hammer. The entire system is so constructed, configured and connected as to permit the heating of the loop to a temperature sufficient to soften thermoplastic bone cement and, while heated, to be inserted into the cement by force applied through the probe. Thereafter the loop is cooled embedded in the cement and the cement removing force is applied. The removal force is preferably a striking impact force such as is achieved by a slide hammer or the like.

In one sense, the invention is an improvement in methods and means for removing thermoplastic bone cement from a bone by applying a heated tool to the bone cement. The improvement comprises a substantially rigid support mounting a loop of heating wire to permit electrical heating the tip to a temperature sufficient to melt bone cement, to permit the tip, which may be a loop or molly-bolt assembly or an equivalent structure, be inserted into the bone cement while heated. The loop is then permitted to be cooled to thereby become embedded in the bone cement. The molly-bolt may also be cooled, but need not be. A pulling removing force is then applied through the tip to the cement in which it is embedded to remove the cement from the bone by the application of such force.

One of the advantages of the invention is that, in a preferred embodiment, it is a self-contained, sterilizable thermoplastic bone cement removal system. The system comprises an elongate probe having proximal and distal ends, the proximal end constructed and configured to be inserted into a bone containing such cement to be removed. A loop of heating wire is substantially rigidly mounted in and extending from the proximal end of the probe. Means for supplying electric activating energy to the loop to heat the loop to a temperature sufficient to soften the cement to be removed, and means for exerting a pulling removal force through the probe and the loop and to the cement to be removed are provided in the system. The probe, loop, electric means and force exerting means are constructed and configured to selectively heat the heating element to a temperature sufficient to soften said bone cement and to permit the loop to cool embedded in the bone cement. The removal means is constructed and configured, and arranged, with the probe to apply through the probe a pulling force to the loop embedded in the cement for removing such cement from such bone.

Many variations will come to mind based on a knowledge of the device as described or upon the principles of the invention as disclosed all without departing from the invention.

INDUSTRIAL APPLICATION

This invention has applicability in the manufacture of surgical instruments and in surgery.

What is claimed:

1. An instrument assembly for removing, as a single piece, a mass of previously formed thermoplastic bone cement from a bone in a patient, said instrument assembly being an elongate structure having proximal and distal ends and being constructed and configured to be grasped by the user during use, said elongate structure comprising;

a heater tip assembly forming the proximal end of the elongate structure, said heater tip assembly being constructed and configured to be inserted proximate a bone of a patient from which a mass of thermoplastic bone cement is to be removed and comprising:

an elongate probe having proximal and distal ends; and
an electrical resistivity heater tip rigidly mounted on the proximal end of said elongate probe;

a striker secured to the elongate probe distally from the heater tip;

an electrical system for supplying electricity to the heater tip assembly for heating the heater tip; and hammer means, mounted for movement distally relative to the heater tip assembly, when the instrument is in use, for impacting the striker, the striker being so constructed and secured as part of the instrument assembly that force applied to the striker is applied through the instrument assembly to the heater tip assembly, said hammer means being constructed and configured for applying a removal force to the striker and through the instrument to the heater tip assembly;

the electrical system comprising electrical conductors and means for selectively connecting electricity through said electrical conductors to the heater tip, the electrical resistance of said conductors being so low relative to the electrical resistance of the heater tip that heating occurs substantially only in the heater tip;

the electrical system being constructed, configured and connected, when the instrument assembly is in use, as to heat the heater tip to a temperature sufficient to soften thermoplastic bone cement; the instrument being so constructed and configured as to permit the user to force the heated tip into the mass of thermoplastic bone cement to be removed from the patient and, after permitting the thermoplastic bone cement to cool to a solid, to impact the striker with the hammer means for apply a pulling force through the heater tip to the solid mass of thermoplastic bone cement in which the heater tip is embedded to thereby remove said mass of thermoplastic bone cement substantially as one piece from the patient;

said elongate structure comprising an elongate shaft having proximal and distal ends, the proximal end secured to the probe and the shaft extending from the distal end of the probe, and wherein the hammer means is slidably received on said shaft and the hammer means and probe, respectively, comprise electrical contacts for applying electricity to the heater tip only when said hammer means is positioned adjacent the distal end of said shaft.

2. An instrument assembly for removing, as a single piece, a mass of previously formed thermoplastic bone cement from a bone in a patient, said instrument assembly being an elongate structure having proximal and distal ends and being constructed and configured to be grasped by the user during use, said elongate structure comprising;

a heater tip assembly forming the proximal end of the elongate structure, said heater tip assembly being constructed and configured to be inserted proximate a bone of a patient from which a mass of thermoplastic bone cement is to be removed and comprising:

an elongate probe having proximal and distal ends; and
an electrical resistivity heater tip rigidly mounted on the proximal end of said elongate probe;

a striker secured to the elongate probe distally from the heater tip;

an electrical system for supplying electricity to the heater tip assembly for heating the heater tip; and hammer means, mounted for movement distally relative to the heater tip assembly, when the instrument is in use, for impacting the striker, the striker being so constructed and secured as part of the instrument assembly that force applied to the striker is applied through the instrument assembly to the heater tip assembly, said hammer means being constructed and configured for applying a removal force to the striker and through the instrument to the heater tip assembly;

the electrical system comprising electrical conductors and means for selectively connecting electricity through said electrical conductors to the heater tip, the electrical resistance of said conductors being so low relative to the electrical resistance of the heater tip that heating occurs substantially only in the heater tip;

the electrical system being constructed, configured and connected, when the instrument assembly is in use, as to heat the heater tip to a temperature sufficient to soften thermoplastic bone cement; the instrument being so constructed and configured as to permit the user to force the heated tip into the mass of thermoplastic bone cement to be removed from the patient and, after permitting the thermoplastic bone cement to cool to a solid, to impact the striker with the hammer means for apply a pulling force through the heater tip to the solid mass of thermoplastic bone cement in which the heater tip is embedded to thereby remove said mass of thermoplastic bone cement substantially as one piece from the patient;

said heater tip comprising nichrome wire of about 14 to about 18 gauge having first and second ends, said ends being so secured as to be carried by the proximal end of the probe, at least a portion of said wire extending generally perpendicularly from the axis of the probe.

3. An instrument assembly for removing, as a single piece, a mass of previously formed thermoplastic bone cement from a bone in a patient, said instrument assembly being an elongate structure having proximal and distal ends and being constructed and configured to be grasped by the user during use, said elongate structure comprising;

a heater tip assembly forming the proximal end of the elongate structure, said heater tip assembly being constructed and configured to be inserted proximate a bone of a patient from which a mass of thermoplastic bone cement is to be removed and comprising:

an elongate probe having proximal and distal ends; and
an electrical resistivity heater tip rigidly mounted on the proximal end of said elongate probe;

a striker secured to the elongate probe distally from the heater tip;

an electrical system for supplying electricity to the heater tip assembly for heating the heater tip; and hammer means, mounted for movement distally relative to the heater tip assembly, when the instrument is in use, for impacting the striker, the striker being so constructed and secured as part of the instrument assembly that force applied to the striker is applied through the instrument assembly to the heater tip assembly, said hammer means being constructed and configured for applying a removal force to the striker and through the instrument to the heater tip assembly;

the electrical system comprising electrical conductors and means for selectively connecting electricity through said electrical conductors to the heater tip, the electrical resistance of said conductors being so low relative to the electrical resistance of the heater tip that heating occurs substantially only in the heater tip;

the electrical system being constructed, configured and connected, when the instrument assembly is in use, as to heat the heater tip to a temperature sufficient to soften thermoplastic bone cement; the instrument being so constructed and configured as to permit the user to force the heated tip into the mass of thermoplastic bone cement to be removed from the patient and after permitting the thermoplastic bone cement to cool to a solid, to impact the striker with the hammer means for apply a pulling force through the heater tip to the solid mass of thermoplastic bone cement in which the heater tip is embedded to thereby remove said mass of thermoplastic bone cement substantially as one piece from the patient;

said heater tip comprising a pair of tip supports extending from the proximal end of the probe and heater wire forming a bridge portion between the tip supports, the bridge portion being so constructed and configured as to form a cutting edge portion.

4. The instrument assembly of claim 3 wherein the bridge portion of the wire has a smaller transverse cross-section than the transverse cross-section of the tip supports.

5. The instrument assembly of claim 3 wherein the tip supports are spaced from about 0.2 to about 0.4 inch apart and are substantially straight.

6. An instrument assembly for removing, as a single piece, a mass of previously formed thermoplastic bone cement from a bone in a patient, said instrument assembly being an elongate structure having proximal and distal ends and being constructed and configured to be grasped by the user during use, said elongate structure comprising;

a heater tip assembly forming the proximal end of the elongate structure, said heater tip assembly being constructed and configured to be inserted proximate a bone of a patient from which a mass of thermoplastic bone cement is to be removed arid comprising:

an elongate probe having proximal and distal ends; and an electrical resistivity heater tip rigidly mounted on the proximal end of said elongate probe;

a striker secured to the elongate probe distally from the heater tip;

an electrical system for supplying electricity to the heater tip assembly for heating the heater tip; and hammer means, mounted for movement distally relative to the heater tip assembly, when the instrument is in use, for impacting the striker, the striker being so constructed and secured as part of the instrument assembly that force applied to the striker is applied through the instrument assembly to the heater tip assembly, said hammer means being constructed and configured for applying a removal force to the striker and through the instrument to the heater tip assembly;

the electrical system comprising electrical conductors and means for selectively connecting electricity through said electrical conductors to the heater tip, the electrical resistance of said conductors being so low relative to the electrical resistance of the heater tip that heating occurs substantially only in the heater tip;

the electrical system being constructed, configured and connected, when the instrument assembly is in use, as to heat the heater tip to a temperature sufficient to soften thermoplastic bone cement; the instrument being so constructed and configured as to permit the user to force the heated tip into the mass of thermoplastic bone cement to be removed from the patient and, after permitting the thermoplastic bone cement to cool to a solid, to impact the striker with the hammer means for apply a pulling force through the heater tip to the solid mass of thermoplastic bone cement in which the heater tip is embedded to thereby remove said mass of thermoplastic bone cement substantially as one piece from the patient;

said elongate structure comprising an elongate shaft having proximal and distal ends, the proximal end secured to the probe extending distally from the distal end of the probe, and wherein the hammer means is slidably received on said shaft and comprises the electrical system, said electrical system comprising one or more electric cells, said striker comprising means at the distal end of the shaft for stopping the slidable movement of said hammer means.

7. The instrument assembly of claim 6 wherein said hammer means and probe, respectively, comprise electrical contacts for applying electricity to the heater tip only when said hammer is positioned adjacent the distal end of the probe.

8. The instrument assembly for removing mass of thermoplastic bone cement of claim 7 wherein the heater tip comprises nichrome wire of about 14 to about 18 gauge having first and second ends, said ends being so secured as to be carried by the proximal end of the probe, at least a portion of said wire extending generally perpendicularly from the axis of the probe.

9. The instrument assembly of claim 7 wherein the heater tip comprises a pair of tip supports extending from the proximal end of the probe and heater wire forming a bridge portion between the tip supports, the bridge portion being so constructed and configured as to form a cutting edge portion.

10. The instrument assembly of claim 9 wherein the bridge portion of the wire has a smaller transverse cross-section than the transverse cross-section of the tip supports.

11. The instrument assembly of claim 6 wherein the tip supports are spaced from about 0.2 to about 0.4 inch apart and are substantially straight.

12. The instrument assembly of claim 6 wherein the probe has an axis and wherein the tip extensions extend substantially parallel to the axis of the probe.

13. The instrument assembly of claim 6 wherein the probe has an axis and wherein the tip extensions extend generally transversely to the axis of the probe.

14. The instrument assembly of claim 6 wherein the heater supports comprise means on the surface thereof and extending outwardly to provide greater gripping power.

15. The instrument assembly of claim 1 wherein the heater tip comprises a molly-bolt sleeve and an enlarged bead at the end of the probe, the molly-bolt sleeve being slidably received on the probe closely adjacent the bead.

16. A self-contained thermoplastic bone cement removal system comprising, in combination: an elongate probe having proximal and distal ends, the proximal end constructed and configured to be inserted into a bone containing such cement to be removed; a heater tip substantially rigidly mounted in and extending from the proximal end of the probe; a hammer shaft connected to the distal end of the probe, electric means comprising electric cells and means for selectively connecting said cells electrically to the heater tip for heating the heater tip to a temperature sufficient to soften the cement to be removed, and means for exerting a removal force through the probe and the heater tip and to the cement to be removed, the means for exerting a removal force comprising a plurality of said electric cells bundled together and slidably mounted on said hammer shaft to form a hammer, the probe, heater tip, electric means and force exerting means being constructed and configured to selectively heat the heater tip to a temperature sufficient to soften said bone cement and, after permitting the bone cement to cool to a solid mass, to apply through the probe a pulling removing force to the heater tip embedded in the cement for removing such mass of cement from such bone.

17. A method for removing as a single piece a mass of thermoplastic bone cement formed previously in a bone from said bone comprising the steps of:

a) heating by electrical current flow through a resistivity electrical heater loop to a temperature sufficient to soften a portion of the previously formed thermoplastic bone cement mass to be removed, said heater loop being substantially rigidly mounted to and extending from the end of an elongate probe, said loop being heated substantially independently of the probe;

b) inserting the heated heater loop into the previously formed mass of thermoplastic bone cement by melting only a portion of the previously formed mass of thermoplastic bone cement;

c) allowing the heater loop to cool in the melted portion of the previously formed mass of thermoplastic cement to form a solid mass comprising the melted and cooled and the unmelted portions of previously formed thermoplastic bone cement with the heater loop embedded therein; and thereafter d) pulling the heater loop thereby removing substantially all of the solid mass formed of said melted and cooled and unmelted portions of bone cement as a single mass.

* * * * *